US007000261B1

(12) United States Patent
Loffredo

(10) Patent No.: US 7,000,261 B1
(45) Date of Patent: Feb. 21, 2006

(54) OSTOMY BAG SUPPORT GARMENT

(76) Inventor: Anna Loffredo, 146 Amsterdam Ave., Hawthorne, NY (US) 10532

( * ) Notice: Subject to any disclaimer, the term of this patent is extended or adjusted under 35 U.S.C. 154(b) by 0 days.

(21) Appl. No.: 10/963,133

(22) Filed: Oct. 12, 2004

(51) Int. Cl.
A41D 13/00 (2006.01)
(52) U.S. Cl. .................. 2/400; 2/228; 2/238
(58) Field of Classification Search .............. 2/400, 2/403–407, 227, 228, 238, 247–251, 234, 2/235, 79, 69, 73, 78.1–78.4
See application file for complete search history.

(56) References Cited

U.S. PATENT DOCUMENTS

| 2,583,721 | A | * | 1/1952 | Beede | 604/345 |
| 3,324,856 | A | * | 6/1967 | Young | 604/394 |
| 3,468,310 | A | | 9/1969 | Kimball | |
| 4,145,763 | A | | 3/1979 | Abrams et al. | |
| 4,533,355 | A | | 8/1985 | Fair | |
| 4,675,918 | A | | 6/1987 | O'Brien | |
| 5,135,520 | A | | 8/1992 | Beaupied | |
| 5,174,305 | A | | 12/1992 | Childs | |
| 5,315,716 | A | | 5/1994 | Baum | |
| 5,706,523 | A | | 1/1998 | Witzel | |
| 6,110,156 | A | * | 8/2000 | Mendonca | 604/345 |
| 6,202,222 | B1 | * | 3/2001 | Robbins | 2/406 |
| 6,468,254 | B1 | * | 10/2002 | Gupton | 604/345 |

* cited by examiner

Primary Examiner—Gloria M. Hale
(74) Attorney, Agent, or Firm—McGlew & Tuttle, P.C.

(57) ABSTRACT

A torso portion is shaped to surround a torso of a user. The torso portion has an inside and an outside, as well as a leg end and a waist end. A pocket is connected to the inside of the torso portion, where the pocket has first and second sides arranged on diametrically opposite sides of the pocket. A first opening is arranged in the torso portion closer to the first side of the pocket than the second side. The first opening extends from the inside to the outside of the torso portion. A second opening is arranged in the torso portion closer to the second side of the pocket than the first side. The second opening also extends from the inside to the outside of the torso portion.

18 Claims, 5 Drawing Sheets

OSTOMY BAG SUPPORT GARMENT

FIELD OF THE INVENTION

The present invention relates to a garment for supporting an ostomy bag, and in particular to an undergarment with openings allowing easy access to a pocket holding an ostomy bag, and openings allowing easy donning and removing of the undergarment.

BACKGROUND OF THE INVENTION

Individuals undergoing ostomy type surgical operations have an outside opening or stoma in the skin of their body, which is then usually connected to an ostomy bag for receiving wastes from the body. This stoma is usually in the front lower torso area of the body. The stoma is usually a very delicate device, and does not have sufficient strength to support an ostomy bag. Many garments are known which can be worn by the individual to support an ostomy bag. U.S. Pat. Nos. 3,468,310, 4,533,355, 5,135,520, 6,110,156, and 6,468,254 describe such garments and are hereby incorporated by reference.

The stoma and ostomy bag on the individual often needs to be accessed for inspection, maintenance, cleaning, and connection/disconnection of the ostomy bag from the stoma. The stoma is often very delicate and applicant has found that moving an ostomy support garment to gain access to the stoma and/or ostomy bag can often be difficult and cause injury to the individual or user of the garment. Also, very often the user of the garment has had the ostomy type surgical operations because of a more serious physical disability. These additional physical disabilities can make it additionally difficult to access the ostomy bag and/or stoma. Many garments are known which allow easy donning and removal of the garments or access to the portion of the body covered by the garment. U.S. Pat. Nos. 4,145,763, 4,675,918, 5,174,305, 5,315,716, and 5,706,523 describe such garments and are hereby incorporated by reference.

However the above cited prior art does not teach nor suggest an ostomy bag support garment where it is as easy to access the stoma and ostomy bag as in the present invention.

SUMMARY OF THE INVENTION

It is an object of the present invention to provide a garment with good support for an ostomy bag and also provide easy access to the ostomy bag, as well as have the garment be easy to don and remove.

The present invention accomplishes this by providing the garment with a torso portion shaped to surround a torso of the user. The torso portion has an inside and an outside, as well as a leg end and a waist end. A pocket is connected to the inside of the torso portion, where the pocket has first and second sides arranged on diametrically opposite sides of the pocket. A first opening is arranged in the torso portion closer to the first side of the pocket than the second side. The first opening extends from the inside to the outside of the torso portion. A second opening is arranged in the torso portion closer to the second side of the pocket than the first side. The second opening also extends from the inside to the outside of the torso portion.

By providing two openings on opposite sides of the pocket, access to the pocket is greatly increased. When the two openings are open, the part of the torso portion holding the pocket can be folded out to provide a plentiful amount of room around the pocket and the ostomy bag inside the pocket. This folding out also provides lots of room for accessing the portion of the user having the stoma. If even further access is desired, one of the openings is shaped to extend completely from and through the waist end to and through the leg end. This allows almost the entire leg area to be accessible without having to remove the garment completely. Further ease in donning and removing the garment can be obtained by providing a third opening on the other leg area of the garment. When the first and third openings are completely open, the garment can be donned and removed, much like a diaper, without having to pass the user's legs through the garment. This avoids having to move the patient significantly.

The pocket fasteners allow the pocket to be removed from garment. If the pocket becomes soiled, the pocket can be removed from the garment and washed separately, or a new pocket installed. This avoids the difficulty of removing the entire garment from the user when just the pocket is dirty. This is especially beneficial when the user is additionally handicapped, such as when the patient is confined to a wheel chair or is bedridden.

The stoma can be located in different areas of the user. Additional pocket fasteners can be arranged in different areas of the garment where stomas are likely. In particular, pocket fasteners can be arranged on the right and left leg portions of the garment. The pocket can therefore be moved from the right to left legs. The additional pocket fasteners can also be arranged higher and lower on the garment to adjust for different vertical positions of the stoma on the user.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
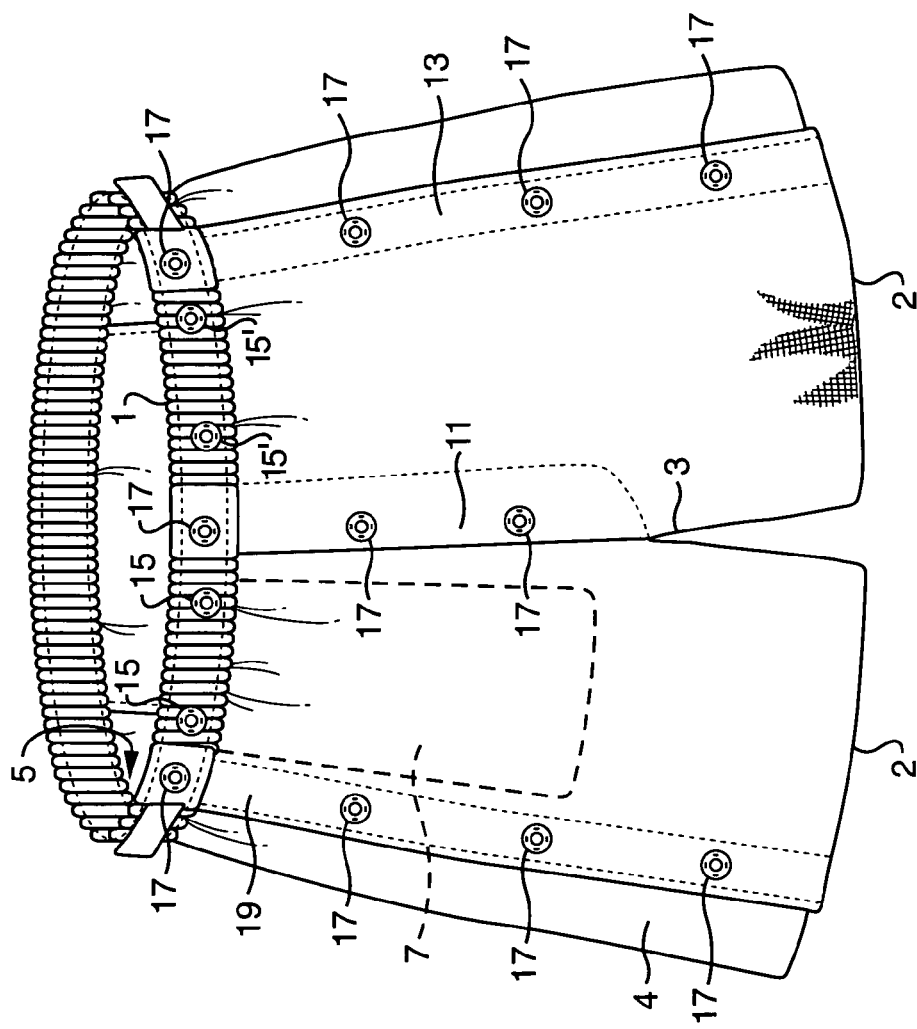
FIG. 1 is a front view of the garment of the present invention where the openings are all closed.

Referring to the drawings, and in particular to FIG. 1, a garment is shown which has a torso portion shaped to surround a torso of a user, and including a waist end 1 and a leg end 2. The user of the undergarment can be male or female. The torso portion has an outside 4 and an inside 5. The torso portion is preferably formed in the boxer style of undergarments because of the loose-fitting arrangement which comfortably provides space for the ostomy bag.

However, other possible styles of undergarments are possible depending on the needs of the user.

A pocket 7 is arranged on the inside 5 of the torso portion. This pocket 7 is preferably shaped to hold the ostomy bag of the user. The pocket 7 is preferably formed of waterproof/water-resistant material that is compatible and comfortable with the skin of the user. The pocket 7 can be arranged on the right or left side of the torso portion depending on where the stoma of the patients is located. The pocket 7 is preferably attached to the torso portion by pocket fasteners 15. These pocket fasteners 15 are designed to be repetitively connectable and disconnectable without significantly damaging or destroying the pocket fasteners 15, the pocket 7 or the fabric of the garment. The pocket fasteners 15 can be snaps, buttons, zippers, hook and eye fasteners, or any other known fastening devices. An alternate set of pocket fasteners 15' can be provided on the opposite side of the torso portion so the pocket 7 can be selectively moved between the right and left sides of the torso portion. The alternate set of pocket fasteners 15' can also be arranged elsewhere on the garment to place the pocket in a more desirable location.

The torso portion defines a first opening 19 and a second opening 11. The second opening 11 is preferably the standard center opening in a pair of boxer shorts, and is arranged in the front center, stopping short of the crotch portion 3. The first opening 19 is arranged on the other side of the pocket 7. The openings 19 and 11 extend from the inside 5 to the outside 4 of the torso portion. In the preferred embodiment, the first opening 19 also extends completely from, and through, the waist end 1 to, and through, the leg end 2. The second opening 11 also extends from and through the waist end 1.

Figure 2:
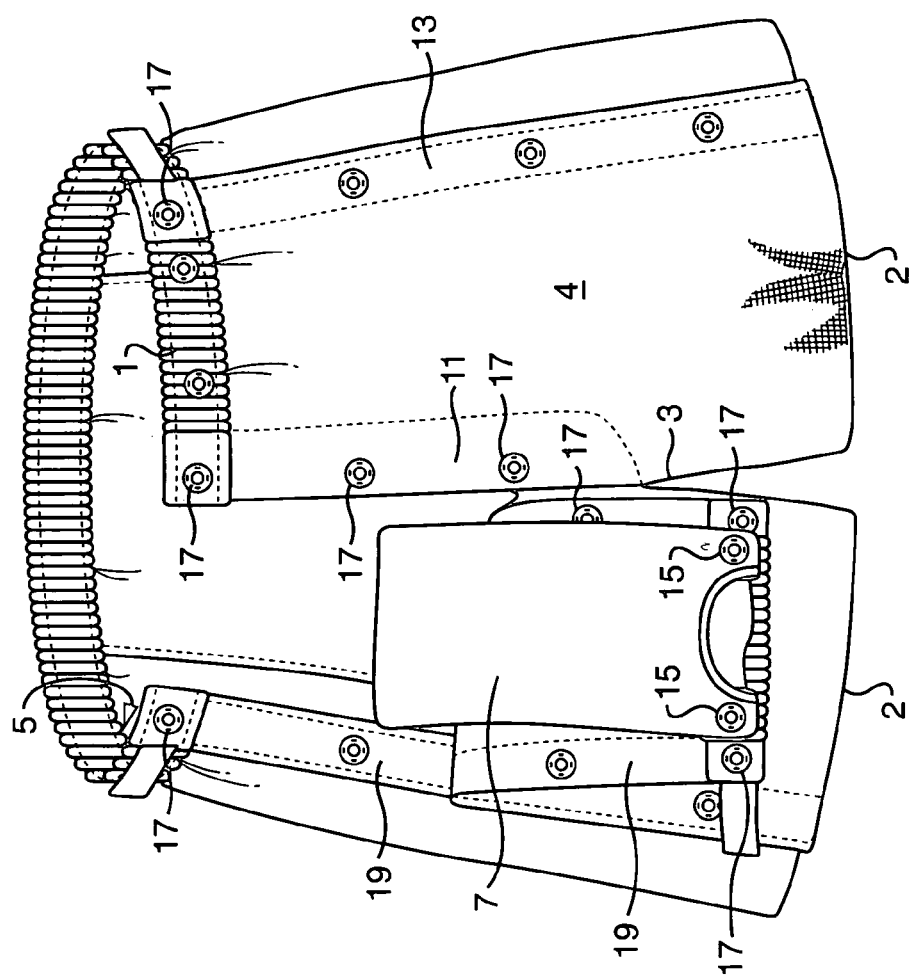
FIG. 2 is a front view of the garment where some of the openings are partially opened allowing access to the pocket holding the ostomy bag.

In order to gain access to the pocket 7 and the enclosed ostomy bag, the openings 19 and 11 are opened and the part of the torso portion holding the pocket 7 is folded out, as shown in the arrangement of FIG. 2. The openings 19 and 11 are selectively opened and closed by fasteners 17 which are designed to be repetitively connectable and disconnectable without significantly damaging or destroying the opening fasteners or the garment. The opening fasteners 17 can be snaps, buttons, zippers, hook and eye fasteners, or any other known fastening devices.

Figure 3:
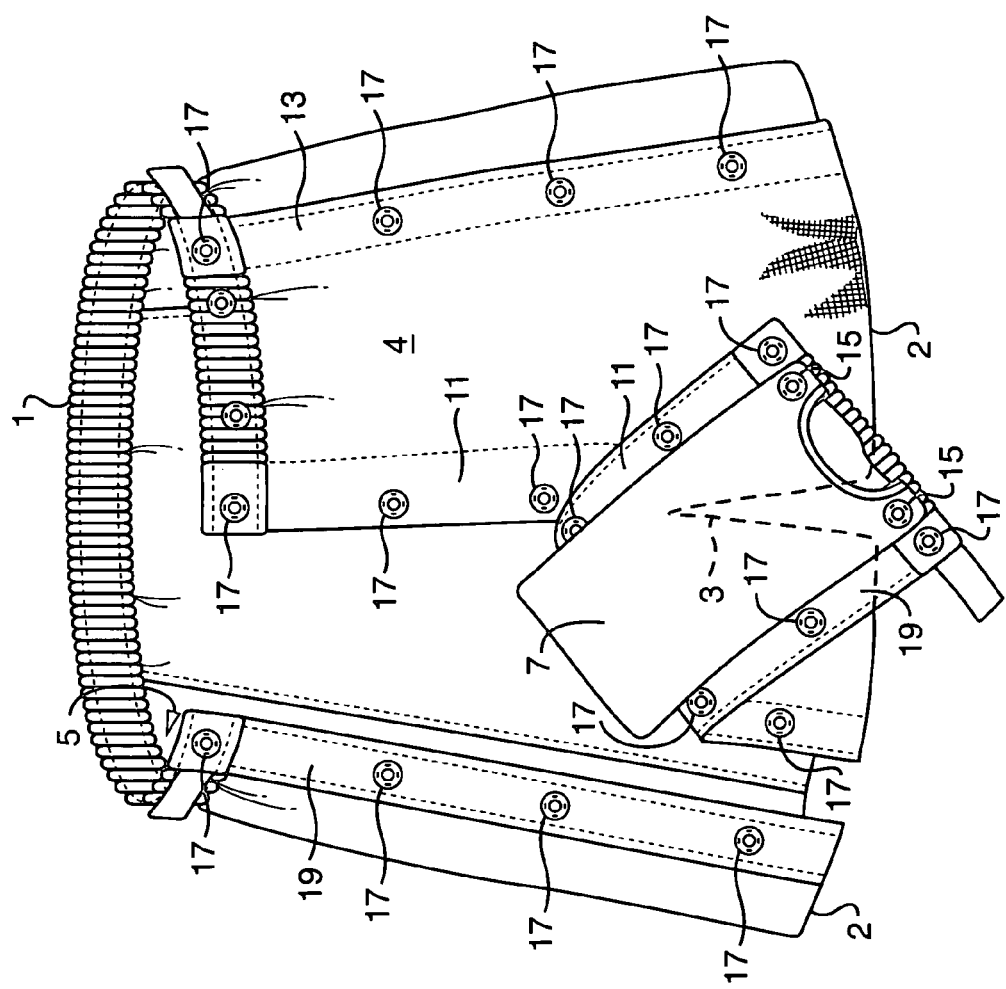
FIG. 3 is a front view of the garment where one of the openings is fully opened allowing further access to the pocket and to the user.
Figure 4:
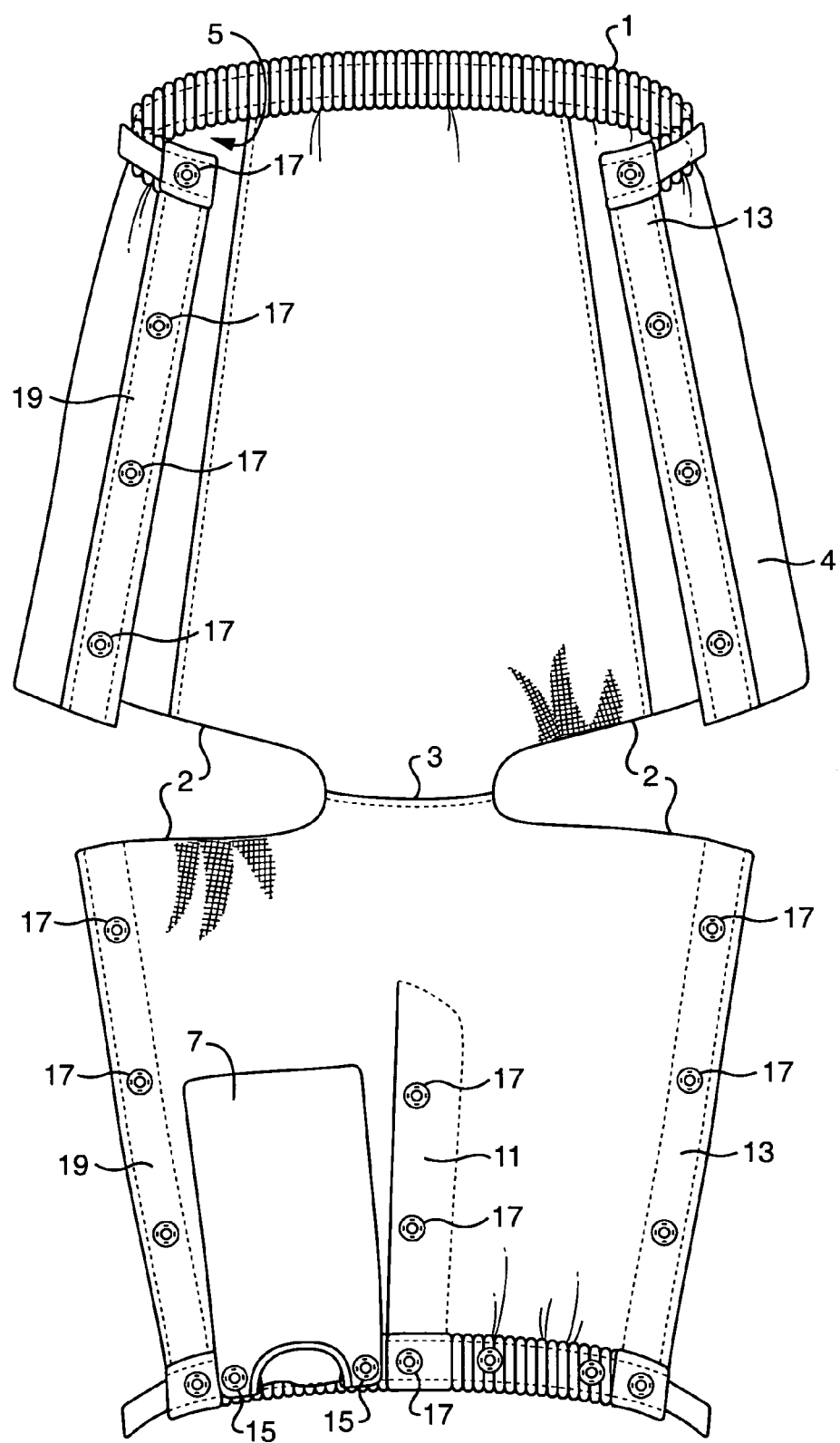
FIG. 4 is a front view of the garment where two of the openings are fully opened allowing greater access to the user and easy donning and removal of the garment.
Figure 5:
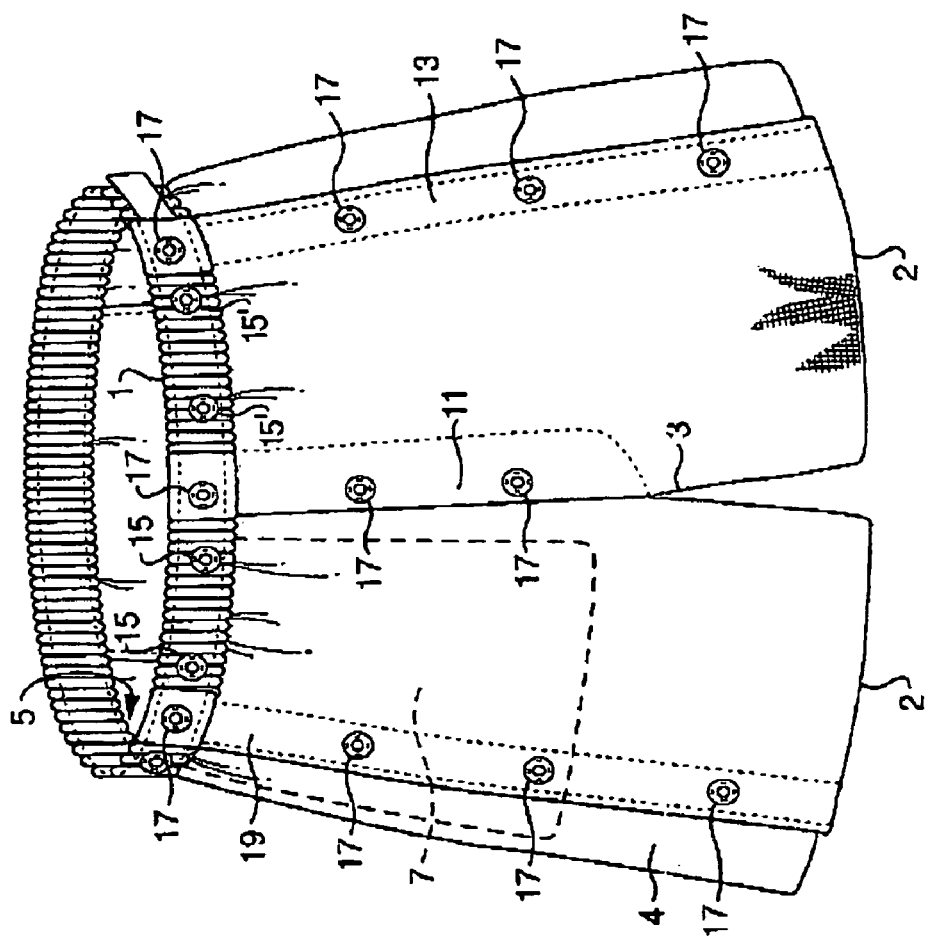
FIG. 5 is a front view of the garment with the pocket extending across an opening.

If further access to the inside 5 of the torso portion is desired, the first opening 19 can be fully opened from the waist end 1 to the leg end 2, as shown in the arrangement of FIG. 3. If still further access to the inside 5 of the torso portion is desired, a third opening 13 is provided which extends from the inside 5 to the outside 4 of the torso portion. This third opening 13 is arranged on the opposite leg portion from the first opening 19. The third opening 13 is also provided with opening fasteners 17. When maximum access is desired to the inside of the torso portion, the first and third openings can be fully opened, preferably from the waist end 1 to the leg end 2. This provides a large degree of access as shown in FIG. 4.

In another embodiment, the pocket 7 can be arranged to extend across the first opening 19. In this embodiment, the pocket 7 would need to be at least partially disconnected from the torso portion in order for the first opening 19 to be opened. Such an arrangement of the pocket 7 and the first opening 19 occur depending on where it is most convenient to place the pocket 7 in relation to the stoma of the user, and where it is most convenient to place the first opening 19 to be opened and closed by the user or the caregiver.

Users who have ostomy bags usually have other disabilities which make the use of the ostomy bag difficult. By the present invention providing first, second and third openings, 19, 11 and 13, where the first and third openings 19 and 13 extend fully from the waist end 1 to the leg end 2, installing, removing and cleaning/maintaining the ostomy bag in the pocket 7 is made easier for the user or caregiver, as well as for donning and removing the undergarment.

While specific embodiments of the invention have been shown and described in detail to illustrate the application of the principles of the invention, it will be understood that the invention may be embodied otherwise without departing from such principles.

What is claimed is:

1. An undergarment comprising:
    a torso portion shaped to surround a torso of a user, said torso portion having an inside and an outside, said torso portion also having a leg end and a waist end;
    a pocket connected to said inside of said torso portion, said pocket having first and second sides arranged on diametrically opposite sides of said pocket;
    a first opening arranged in said torso portion closer to said first side of said pocket than said second side, said first opening extending from said inside to said outside of said torso portion;
    a second opening arranged in said torso portion closer to said second side of said pocket than said first side, said second opening extending from said inside to said outside of said torso portion;
    pocket fasteners repetitively connecting and disconnecting said pocket from said torso portion without substantially damaging said pocket or said torso portion.

2. An undergarment in accordance with claim 1, wherein:
    said first and second openings extend through said waist end of said torso portion.

3. An undergarment in accordance with claim 1, wherein:
    said first opening extends through said leg end of said torso portion.

4. An undergarment in accordance with claim 1, wherein:
    said first opening extends completely from said waist end to said leg end of said torso portion.

5. An undergarment in accordance claim 1, further comprising:
    opening fasteners arranged around said first and second openings, said opening fasteners repetitively opening and closing respective said first and second openings without substantially damaging said torso portion.

6. An undergarment in accordance with claim 2, wherein:
    said torso portion has a front side arranged to be worn on a front of the torso of the user, said second opening is arranged substantially centered on said front side.

7. An undergarment in accordance with claim 6, wherein:
    said first opening extends completely from said waist end to said leg end of said torso portion;
    said second opening is spaced from said leg end of said torso portion.

8. An undergarment in accordance with claim 1, wherein:
    said torso portion includes a crotch portion arranged at said leg end and shaped to fit a crotch of the user.

9. An undergarment in accordance with claim 1, wherein:
    said torso portion defines a third opening extending completely from said waist end to said leg end of said torso portion, said third opening being arranged on a side of said second opening diametrically opposite said first opening.

10. An undergarment in accordance with claim 9, wherein:
    said torso portion includes a crotch portion arranged at said leg end and shaped to fit a crotch of the user, said first and third openings being arranged on diametrically opposite sides of said crotch portion.

11. An undergarment in accordance with claim 1, wherein:
   said pocket is formed to be primarily supportive of a colostomy bag and compatible with a skin of the user.

12. An undergarment in accordance with claim 1, wherein:
   said torso portion is formed to be loose fitting to the torso of the user.

13. An undergarment in accordance with claim 1, wherein:
   said pocket is arranged between said first and second openings.

14. An undergarment in accordance with claim 1, wherein:
   said pocket extends across said first opening.

15. An undergarment in accordance with claim 1, further comprising:
   additional pocket fasteners arranged on the torso portion, said pocket being selectively connectable to said pocket fasteners and said additional pocket fasteners.

16. An undergarment in accordance with claim 1, wherein:
   said first opening extends completely from said waist end to said leg end of said torso portion;
   opening fasteners are arranged around said first and second openings, said opening fasteners repetitively opening and closing respective said first and second openings without substantially damaging said torso portion or said opening fasteners;
   said torso portion has a front side arranged to be worn on a front of the torso of the user, said second opening is arranged substantially centered on said front side;
   said torso portion includes a crotch portion arranged at said leg end and shaped to fit a crotch of the user, said crotch portion being shaped to fit a crotch of the user;
   said second opening is spaced from said crotch portion of said torso portion;
   said torso portion defines a third opening extending completely from said waist end to said leg end of said torso portion, said third opening being arranged on a side of said second opening diametrically opposite said first opening;
   said first and third openings are arranged on diametrically opposite sides of said crotch portion;
   said pocket is formed to be primarily supportive of a colostomy bag and compatible with a skin of the user;
   said torso portion is formed to be loose fitting to the torso of the user;
   said pocket is arranged between said first and second openings;
   additional pocket fasteners are arranged on the torso portion, said pocket being selectively connectable to said pocket fasteners and said additional pocket fasteners.

17. An undergarment comprising:
   a torso portion shaped to surround a torso of a user, said torso portion having an inside and an outside, said torso portion also having a leg end and a waist end;
   a pocket connected to said inside of said torso portion, said pocket having first and second sides arranged on diametrically opposite sides of said pocket;
   a first opening arranged in said torso portion closer to said first side of said pocket than said second side, said first opening extending from said inside to said outside of said torso portion, said pocket extending across said first opening;
   a second opening arranged in said torso portion closer to said second side of said pocket than said first side, said second opening extending from said inside to said outside of said torso portion.

18. An undergarment comprising:
   a torso portion shaped to surround a torso of a user, said torso portion having an inside and an outside, said torso portion also having a leg end and a waist end;
   a pocket connected to said inside of said torso portion with pocket fasteners, said pocket having first and second sides arranged on diametrically opposite sides of said pocket;
   a first opening arranged in said torso portion closer to said first side of said pocket than said second side, said first opening extending from said inside to said outside of said torso portion;
   a second opening arranged in said torso portion closer to said second side of said pocket than said first side, said second opening extending from said inside to said outside of said torso portion;
   additional pocket fasteners arranged on the torso portion, said pocket being selectively connectable to said pocket fasteners and said additional pocket fasteners.

\* \* \* \* \*